(12) United States Patent
Panzner et al.

(10) Patent No.: US 7,763,275 B2
(45) Date of Patent: Jul. 27, 2010

(54) NANOCAPSULES HAVING A POLYELECTROLYTE ENVELOPE

(75) Inventors: Steffen Panzner, Halle (DE); Gerold Endert, Halle (DE); Frank Essler, Halle (DE); Anja Behrens, Leipzig (DE); Silke Lutz, Halle (DE); Cornelia Panzner, Halle (DE)

(73) Assignee: Novosom AG, Halle (DE)

( * ) Notice: Subject to any disclaimer, the term of this patent is extended or adjusted under 35 U.S.C. 154(b) by 452 days.

(21) Appl. No.: 10/220,590

(22) PCT Filed: Mar. 2, 2001

(86) PCT No.: PCT/EP01/02397

§ 371 (c)(1),
(2), (4) Date: Sep. 3, 2002

(87) PCT Pub. No.: WO01/64330

PCT Pub. Date: Sep. 7, 2001

(65) Prior Publication Data

US 2003/0157181 A1 Aug. 21, 2003

(30) Foreign Application Priority Data

Mar. 2, 2000 (DE) .............................. 100 10 264

(51) Int. Cl.
*A61K 9/127* (2006.01)
*A61K 9/50* (2006.01)
(52) U.S. Cl. ..................... 424/450; 424/489; 424/497

(58) Field of Classification Search ................. 424/450, 424/489–502, 417, 420, 1.21, 9.321, 9.51; 264/4.1, 4.3, 4.6; 428/402.2
See application file for complete search history.

(56) References Cited

U.S. PATENT DOCUMENTS

| 6,077,887 A | * | 6/2000 | Thuresson | 524/42 |
| 6,713,533 B1 | * | 3/2004 | Panzner | 523/202 |
| 2003/0219384 A1 | | 11/2003 | Donath et al. | 424/9.6 |

FOREIGN PATENT DOCUMENTS

| EP | 0972563 | * | 1/2000 |
| SU | 482093 | * | 5/1978 |
| SU | 482093 | | 6/1978 |
| WO | 99/47252 | * | 9/1999 |

OTHER PUBLICATIONS

Gleb B. Sukhorukov et al., Stepwise Polyelectrolyte Assembly on Particle Surfaces: a Novel Approach to Colloid Design, Polymers for Advanced Technologies, Polym. Adv. Technol. 9, 759-767 (1998).

* cited by examiner

*Primary Examiner*—Gollamudi S Kishore
(74) *Attorney, Agent, or Firm*—Rissman Hendricks & Oliverio, LLP

(57) ABSTRACT

A method for the production of nano- or microcapsules having a diameter of from 20 nm to 40 µm is suggested, wherein template particles are supplied in an aqueous medium, electrically recharged with a polyelectrolyte, re-recharged without separation or washing steps using a second polyelectrolyte having a complementary charge with respect to the first polyelectrolyte, and said process is optionally continued with alternately charged polyelectrolytes.

16 Claims, 2 Drawing Sheets

NANOCAPSULES HAVING A POLYELECTROLYTE ENVELOPE

BACKGROUND OF THE INVENTION

The invention relates to nanocapsules enclosed by a stable coat layer of polyelectrolytes, to a method of producing such structures, and to the use of these structures. The invention also relates to a device for the production of said nanocapsules.

Liposomes are known to be a highly biocompatible form of packaging various active substances. The components of liposomes are tolerable at high doses, triggering no or only slight defensive reactions by the immune system. However, the use of liposomes frequently is opposed by their sensitivity to mechanical, thermal or biological exposure.

The lifetime of liposomes can be extended via the composition of the liposomal membrane; however, this is accompanied by loss of other desirable properties such as fusion competence.

Up to now, numerous efforts have therefore been made to utilize the mild and biocompatible way of packaging by liposomes with the aid of stabilizing additives for uses in pharmacy and industry. A familiar method of increasing the stability of liposomes is doping their surface with various polymers, particularly polyethylene glycol (PEG). These components effect steric shielding of the surface, thus preventing direct attack of lytic components, e.g. from the blood system, on the membrane; e.g. "stealth liposomes" as liposomal preparations wherein the liposomes are enclosed by a coat of PEG (D. D. Lasic, "Liposomes—from physics to applications").

Other well-known methods use protection of the liposomal membrane by coating sugar oligomers on the membrane layer. Similarly, steric shielding of the membrane surface is achieved by the coated components. In contrast to non-modified liposomes, the structures obtained can be frozen or lyophilized.

DE 198 52 928.7 and WO 00/28972 disclose coat structures on liposomal templates, which structures allow versatile modification, they are stable by themselves and can be produced using layer-by-layer chemisorption of polymers or bio-molecules. Apart from producing coat layers and nanocapsules, the method also allows for biocompatible modification and functionalization of the surface.

Alternatively, structures of similar constitution can be produced using layer-by-layer polyelectrolyte self-assembly on colloidal templates (Caruso, F. (1998), Science 282, 1111-1113, DE 198 12 083 A1, EP 0,972,563 A1, and WO 99/47253)

WO 00/03797 discloses the suitability of liposomes and other biological templates as supports for the production of nanocapsules using layer-by-layer self-assembly.

A familiar method of producing such structures is crosslinking of proteins on boundary surfaces (U.S. Pat. No. 5,498,421) or on the surface of liposomes (Kupcu, S., Sara, M., and Sleytr, U. B., Biochem. Biophys. Acta, 1235 (2), 263-269 (1995)).

U.S. Pat. No. 5,308,701 discloses a method which describes inclusion of liposomes, among other things, in microcapsules made up of polyelectrolyte layers. However, the solution described therein avoids binding of the first polyelectrolyte to the lipid layer. Rather, the liposomes in U.S. Pat. No. 5,308,701—like all the other dissolved substances—are micro-encapsulated by a droplet of the surrounding polymerizing material. The liposomes do not act as a template of the micro-capsule; the result is formation of significantly larger capsules including a multitude of liposomes in their gel-like interior. As a result of their size, these micro-capsules are unsuitable for use in the blood circulation.

Furthermore, the well-known basic structures involve the following drawbacks:

U.S. Pat. No. 5,498,421 uses an oil phase as matrix which, as a consequence, allows inclusion of fat-soluble substances only. As a result, use of this system for most biopolymers is impossible.

Being highly immunogenic structures, the S-layer proteins used by Kupcu et al. are unsuitable for use in pharmaceutical carriers.

Furthermore, the disclosed liposomal structures and methods of producing same are disadvantageous due to lacking bio-compatibility and in that dissolution thereof involves extreme conditions such as high temperatures or exceedingly low pH values.

Moreover, the well-known methods use excess polyelectrolyte material to a achieve a preferably dense and reproducible coating on the surface of the nanocapsules or liposomes and therefore, additional process steps are required to remove excess polyelectrolyte material. In addition, there is no disclosure of a method for coating liposomes with polyelectrolytes. The methods proposed in general, e.g. in WO 00/03797, are not feasible due to formation of undissolvable aggregates during the process. Another drawback is that all these processes proceed in a discontinuous fashion, preventing uniform coating of the nanocapsules or liposomes.

SUMMARY OF THE INVENTION

It was therefore the object of the invention to provide an economic method allowing facile production of templates, especially liposomes enclosed by an independent coat layer.

The present invention solves this technical problem by providing nano- or microcapsules having a diameter of between 20 nm and 40 µm, template particles being supplied in an aqueous medium, electrically recharged with a first polyelectrolyte, re-recharged without separation or washing steps using polyelectrolytes of complementary charge, said process optionally being continued with alternately charged polyelectrolytes. The alternating charge of the layers can be generated in such a way that e.g. the first layer is comprised of anionic or predominantly anionic polyelectrolytes and the second layer of cationic or predominantly cationic polyelectrolytes.

Templates in the meaning of the invention are all those templates which can be coated using the method according to the invention. Subsequent to providing the templates, the particles can be coated e.g. in an amphiphilic fashion and coated in a further step with a polyelectrolyte which, in particular, has a charge opposite to that of the surface of the particle materials. In order to form multiple layers, the templates are subsequently treated with polyelectrolytes of opposite charge, i.e. alternately with cationic and anionic polyelectrolytes. The polymer layers undergo self-assembly on the previously charged solid templates by electrostatic deposition in layers, thereby forming a multi-layered polymer coat around the solid cores.

DETAILED DESCRIPTION OF THE PREFERRED EMBODIMENTS

Figure 1:
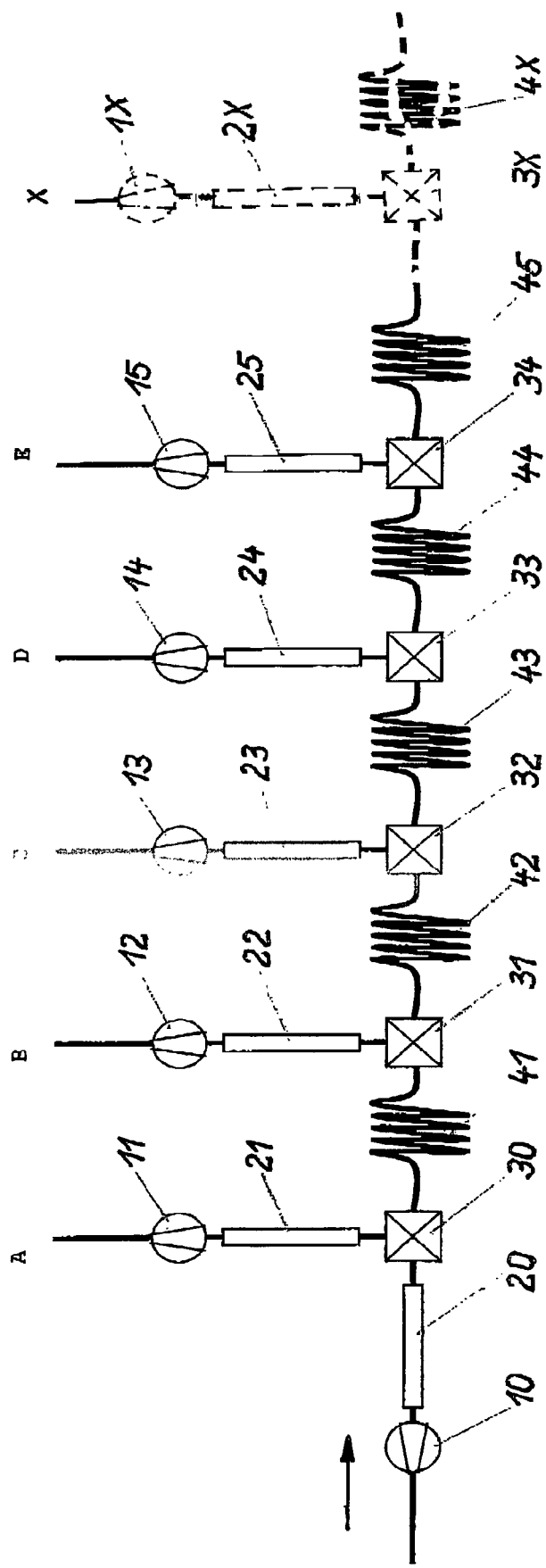
FIG. 1 diagram showing the introduction of polyelectrolytes into a tube used for coating liposomes.

According to the invention, such structures of alternately charged polyelectrolytes can be produced e.g. by coating two or more water-soluble polyelectrolyte layers of complementary charge onto the surface of liposomes which, in particular, are capable of producing electrostatic interactions. The polymer electrolyte layers in direct succession have opposite charges. Any number, but at least two such polymer electrolyte layers can be deposited on the surface of the liposomes. Polyelectrolytes in the meaning of the invention are polymers with groups capable of ionic dissociation, which groups can be components or substituents of the polymer chain, their number being of a level so as to render the polymers water-soluble in their dissociated form. According to the invention, ionomers are concerned in that case where the concentration of ionic groups is insufficient for water solubility. Polymers having not more than one or only a few ionic groups are macroions, e.g. macroanions or macrocations. In the meaning of the invention, the polyelectrolytes are subdivided in polyacids and polybases, depending on the type of dissociable groups. Polyanions which can be both inorganic species and organic polymers are formed from polyacids upon dissociation with abstraction of protons. Examples of polyacids—the salts of which being referred to as polysalts—are the following: polyphosphoric acid, polyvinylsulfuric acid, polyvinylsulfonic acid, polyvinylphosphonic acid, and polyacrylic acid. Polybases include such groups as pro-ionic groups which, inter alia, are capable of accepting protons e.g. by reaction with acids to form salts. Typical polybases with chain or lateral dissociable groups are polyethyleneimine, polyvinylamine and polyvinylpyridine.

In the meaning of the invention, polyelectrolytes including both anionic and cationic groups as substituents on a macromolecule are polyampholytes.

Polyelectrolytes dissociate into polyions and the corresponding counterions. As a rule, they are readily soluble in the aqueous solution of their counterions. In solution, their macromolecules mostly have a linear orientation as a result of electrostatic repulsion between the ionic groups, while in non-dissociated form they are present as coiled molecules. Oligo- and polyvalent counterions induce cross-linking of the polyelectrolytes which may go up to a level resulting in insolubility thereof.

According to the invention, the polyelectrolytes can be biopolymers such as alginic acid, gum arabic, nucleic acids, pectins, proteins, etc., as well as chemically modified biopolymers, e.g. carboxymethylcellulose, ligninsulfonates and synthetic polymers, e.g. poly(meth)acrylic acid, polyvinylsulfonic acid, polyvinylphosphonic acid, polyethyleneimine. Other polyelectrolytes are well-known to those skilled in the art, e.g. from WO 00/28972 or WO 00/03797, the contents thereof being incorporated in the disclosure of the invention.

For example, both structure-forming and activity-bearing polymers can be used to build up the polyelectrolyte layer. The coats may have binding properties for other molecules or catalytic properties, for example. The polymers with structure-forming and activity-bearing properties can be found e.g. among proteins. According to the invention, it is possible to utilize e.g. hemoglobin to build up the coat structure. Thus, the nanocapsules of the invention can be used as blood substitute. However, it is also possible to integrate proteins in the polyelectrolyte layer which are capable of recognizing and binding characteristic structures of other proteins. In particular, suitable proteins for this purpose are lectins as well as proteins binding biotin or antibodies. Such nanocapsules are capable of recognizing glycosylations, antigenic epitopes or biotin groups on proteins or other macromolecules, binding these components in a highly specific manner.

As starting material, liposomes or template particles can be used, the size of which determining the size of the nanocapsules being formed. Suitable methods of producing such liposomes are well-known to those skilled in the art. According to the invention, the liposomes used must enable binding of the water-soluble polymer, in particular. Methods of covalent coupling in aqueous media are well to those skilled in the art and involve, among other things, heterofunctional and homofunctional linkage of amino, thiol, hydrazo, hydroxo, acidic hydrogen, aldehyde, and carboxyl groups, or activated esters thereof in suitable combinations.

As a result of the characteristics of the lipid layer, the interaction between the liposome and the first polyelectrolyte may differ from the preferred electrostatic interactions between succeeding layers. One possible embodiment of the teaching according to the invention therefore involves using such amphipatic polymers or polyelectrolytes which, in combination with a lipid layer, yield a charged particle. Examples of such polyelectrolytes are integral or membrane-bound proteins, amphipatic polymers such as alkyl acrylates, alkyl-modified sugar polymers, and other such substances of natural or synthetic or semi-synthetic origin.

In a succeeding step, a second layer including another polymer is coated on the template particle coated with the first polymer. The charges of the first and second polymer are complementary to each other. First and second polymer form a network on the surface of the liposomes.

The polymers used have a zeta potential other than zero under the reaction conditions. Important quantities to bias this potential comprise the pH value of the solution and the ionic strength. Suitable compounds include a variety of polyelectrolytes, as well as other water-soluble polymers with sufficiently polar groups. For example, suitable compounds include: polysaccharides such as alginic acid, chitosan, pectin, hyaluronic acid, polymannuronic acid, polygalacturonic acid, heparin, gum arabic, Indian traganth, xanthan gum, Carragheen, locust bean gum, and the salts of these compounds, as well as carboxylated, aminated, hydrazylated dextrans, starches, levans, inulins, or agaroses.

Other compounds are natural or synthetic proteins or peptides or other homo- or heteropolymers of amino acids, oligonucleotides, DNA or RNA in single-stranded or double-stranded form and in linear or circular-closed form, synthetic polymers such as polyacrylic acids, polyacrylamides, polyacrylic esters, and other polymers of derivatives of acrylic acid, polyvinylpyrrolidones, polyethyleneimines, polystyrenesulfonic acids, polyallylamines, polyphosphazenes, etc. Further compounds are hetero- or block polymers of the above basic monomers. Also included are mixed forms of the above-mentioned compounds, such as glycosylated proteins, proteins modified subsequent to translation, protein complexes with other natural materials, complexes of proteins and nucleic acids, copolymers of sugars and acrylates and related compounds, as far as all of these compounds are to be water-soluble, in particular.

Following two or more coatings, polyelectrolyte-coated nanocapsules are obtained wherein, in particular, a lipid membrane is enclosed by an exterior coat. Advantageously, this coat alters the surface properties of the liposomes, increasing the stability thereof. The stability can be increased further by exposure to chemical crosslinkers, for example.

In particular, the coating reaction according to the method of the invention can be performed quite rapidly and therefore, chemical crosslinkers advantageously can be mixed into the suspension as early as at the beginning of the reaction and conveniently removed from the suspension not before completion of the coating reaction, if essential for subsequent use.

In particular, the method allows completion of the coating reaction within a few seconds, said reaction rarely taking longer than a few minutes.

Suitable crosslinkers are all those compounds specified e.g. in WO 00/28972 and, in particular, those crosslinkers having no or no substantial effect on the electric net charge of the polyelectrolytes.

In particular, the liposomes employed must allow binding of the first water-soluble polymer. Suitable components for producing such liposomes are charged amphipatic compounds which can be incorporated in the lipid layer without destroying same, which is most important. Suitable compounds include natural or synthetic phospholipids and derivatives thereof, particularly phosphatidyl serine, phosphatidyl inositol, phosphatidyl glycerol, or phosphatidic acid, as well as sphingolipids, ceramides, tetraether lipids or other ether lipids, as well as derivatives of cholesterol like cholesterol sulfate, cholesterol hemisuccinate, dimethylaminoethylcarbamoylcholesterol and other such compounds. Suitable compounds also include alkylcarboxylic acids, alkylsulfonic acids, alkylamines, alkylammonium salts, dialkylamines or ammonium compounds like DOTAP or DOTIM, phosphoric esters with long-chain alcohols and other membrane-forming or membrane-bound compounds. Non-charged membrane components such as phosphatidyl choline, phosphatidyl ethanolamine, α-tocopherol, cholesterol etc. can also be used as membrane-forming components.

In particular, both the liposomes and the polymers used have a plurality of charges which ultimately can lead to binding of the components to each other and to the nanocapsules of the invention.

The liposomes may have uni- or multilamellar membrane structures. It is preferred to use uni- or oligolamellar liposomes having a size of between 20 and 1000 nm, preferably between 50 and 500 nm, and more preferably between 70 and 300 nm.

As a result of the rapid succession of individual mixing processes, the aggregation tendency of the mixtures can be reduced with advantage, thereby enabling coating even at higher lipid and polymer concentrations; in particular, preservation of the integrity of the liposomes in the continuous coating process is superior compared to the discontinuous stirring process, for example.

In a preferred embodiment, the mixing chamber is a static micromixer resulting in particularly rapid and uniform mixing, even with small flows of liquid. Suitable mixers have been described in DE 199 25 184 A1.

This variant of the method works largely independently of the nature of liposome or template used in coating. The benefits of rapid, flow-optimized production of nanocapsules without any intermediate step can also be utilized with colloidal liposomes or templates described so far. Advantageously, the method can be used in the production of polyelectrolyte coats on non-stable templates. Thus, for example, it is also possible to stabilize droplets of an oil-in-water emulsion by using this method, In another preferred embodiment of the invention, the liposomes are dissolved subsequent to coating with polyelectrolytes, preferably by leaching with a detergent. Thus, structures in the form of hollow spheres may be formed, wherein the liposomes have been dissolved subsequent to crosslinking. This may result in liberation of polymers that are bound to the lipid layer only, and not to each other, and may give rise to decomposition of insufficiently crosslinked structures. The nanocapsules can be separated from the decomposition products by sedimentation, gel filtration or ultrafiltration.

Suitable detergents to dissolve the interior liposomes are alkylated sugars such as octylglucoside, salts of cholic acid and derivatives thereof, alkylsulfonic acids, polyoxyethylenesorbitol, or similar compounds. The nanometer range nanocapsules in the meaning of the invention therefore are merely comprised of a polymer backbone forming the surface of a sphere. In particular, the shaping liposomes can be removed in such a way that the size of the hollow spheres having formed is determined by the liposomes being used.

Advantageously, the permeability of the coat layer of the nanocapsules can be increased substantially by leaching the liposomes. For example, this process involves the passage of detergent molecules and mixed micelles through the outer coat layer. In the same way, substrates and products of a reaction proceeding in the interior of the hollow sphere can be exchanged. One arrangement for performing such reactions preferably consists of hollow spheres having in their interior enzymatically active substances with high molecular weights, the liposomes of which have been leached by detergents. In particular, suitable substances for such an inclusion are enzymes or ribozymes. However, it is also possible to leach non-bound polymers only, so that the lipid layer is preserved. In that case, only those substances diffusing through the lipid layer can be exchanged. These are amphiphilic molecules such as phenylalanine. In particular, nanocapsules including phenylalanine-4-hydroxylase or phenylalanine ammonia-lyase can be used to decompose particular amino acids in phenylketonuria.

In another preferred embodiment of the invention, the coat layer of polyelectrolytes is subjected to covalent crosslinking with bifunctional reagents subsequent to deposition thereof.

In another advantageous variant of the method, natural or synthetic polymers or mixed forms of these compounds, e.g. polyacids or polybases are used as polyelectrolytes. Inter alia, polyacids are formed in the dissociation of polyanions, and these polyanions can be both inorganic and organic polymers. Polybases include groups which, in particular, are capable of accepting protons.

In another embodiment of the invention, the polyelectrolytes comprise alginic acids, chitosan, nucleic acids, polynucleotides and/or proteins, preferably albumin, hemoglobin, myoglobin, antibodies, proteases, $\alpha_2$-macroglobulin, fibronectin, collagen, vitronectin, protein A, protein G, avidin, streptavidin, concanavalin A, and/or wheat germ agglutinin.

In another variant of the method, active substances are to be enclosed in the nanocapsules. For example, active substances can be biologically or chemically active compounds which, at low concentrations, have a qualitative or quantitative effect on chemical, biochemical, biophysical, and physiological processes, e.g. metabolic processes in living organisms in a way so as to activate or inhibit particular processes. For example, active substances occurring naturally in organisms, such as vitamins or hormones, can be used. However, it is also possible to use exogenic active substances such as biocides.

In another variant of the method, the liposomes are to comprise phosphatidyl serine, phosphatidyl glycerol, phosphatidic acid, sphingolipids, ceramides, tetraether lipids, cholesterol sulfate, cholesterol hemisuccinate, dimethylaminoethylcarbamoylcholesterol, alkylcarboxylic acids, alkylsulfonic acids, alkylamines, alkylammonium salts, dialkylamines, DOTAP, DOTIM, phosphoric esters with long-chain alcohols, phosphatidyl choline, phosphatidyl ethanolamine, and/or α-tocopherol.

In another embodiment of the invention, coating with polymers is performed at a lipid concentration lower than 2 mM. It is preferred to use lipid concentrations lower than 1 mM, more preferably lower than 0.5 mM, and most preferably lower than 0.2 mM. Owing to the dilutions selected, it is possible in an advantageous fashion to suppress formation of aggregates.

In another embodiment, liposomes including 10 to 50 mole-%, preferably 30 to 50 mole-%, and especially 35 to 45 mole-% of charged sterols are to be used in the method.

When using phospholipids, it is convenient to use more than 10 mole-%, preferably more than 40 mole-%, and more preferably more than 60 mole-%.

Advantageously, the amount of deposited polymer and thus, the density of the generated layers can be controlled via the density of charge carriers on the liposome. This finding is surprising in that the charge carriers can be mobile within the liposomal membrane, and relatively low amounts are sufficient for stoichiometric saturation of the polymer. If the charge carriers themselves are membrane-forming substances, e.g. charged phospholipids or derivatives thereof, or charged dialkyls like DOTAP or DOTIM, even higher amounts of charge carriers can be used with advantage. In this event, it is preferred to use amounts of between 10 and 100% of total lipid, more preferably amounts between 40 and 100%, and most preferably amounts between 40 and 80% of the above-mentioned substances. Advantageously, the charge carrier density on the surface can be increased further by using groups with multiple charges, e.g. high amounts of phosphatidic acid with two negative charges, or substituted membrane-bound compounds bearing multiple charges, e.g. conjugates of spermine and sterols, or those of oligopeptides and phospholipids, or those of heparin and lipids, or those of other multifunctional compounds such as oligo- and polycarboxylic acids or oligo- or polyamines and lipids. The transition to lipid/polymer conjugates is fluid, and the examples mentioned can be supplemented easily by a person skilled in the art.

In another embodiment of the invention, coating with polymers is performed at a salt concentration of more than 50 mM.

Advantageously, the density of liposomal charge carriers can be determined via the maximum salt concentration of the solution where complete binding of the polymer to the template still takes place. Performing coating at a salt concentration as high as possible is advantageous for two reasons:

(i) Salt concentrations of more than 50 mM result in significant compacting of highly charged polymers because intramolecular repulsion is reduced, thereby enabling denser packing of polyelectrolytes on the surface.

(ii) Though not invariably, but in many cases, subsequent increase of the salt concentration of the medium results in aggregation of the particles, probably by partial destabilization of the outer polyelectrolyte layer. However, reducing the salt concentration does not do damage.

In particular, the coating reaction—even in the dilutions—requires considerably less time than that to be expected according to the prior art. Such rapid progression of the reaction enables purposeful arrangement of a continuous process.

Surprisingly, it has also been determined in this context that the phase transition temperature of the liposomal membrane has an effect on the reaction rate. Thus, the coating reactions proceed more rapidly when coating the lipid membrane above the phase transition temperature.

In a preferred embodiment of the invention, one reaction cycle is to be completed within less than 20 minutes, preferably within less than five minutes, and more preferably within less than one minute.

In another advantageous embodiment of the invention, a chemical crosslinker is added during the coating reaction or subsequent to completion thereof.

In another preferred embodiment of the invention, the template particles are to have a size of between 20 nm and 1000 nm, preferably between 50 nm and 500 nm, and more preferably between 70 nm and 300 nm.

In another preferred embodiment of the invention, two or more dissimilar polyelectrolytes are coated simultaneously or successively in one layer.

In a preferred embodiment, the template particles are liposomes.

It may be convenient to have the template particles in an oil-in-water emulsion. In particular, it may be convenient if the emulsions include active substances in their oil phase.

In a preferred embodiment of the invention, the nanocapsules additionally have a lipid layer which has the polyelectrolyte layers thereon. For example, the lipid layer can be the outer oil layer of liposomes situated in the nanocapsule.

The invention also relates to structures including lipid layers in the interior thereof; a liquid phase may be present in the interior of said structures. In principle, any liquid, also including suspensions in the meaning of the invention, can be contained in the interior of the nanocapsules. Examples of liquids are water, buffers, fluid aerosols, etc.

It may be convenient if the structures include a water-immiscible oil phase in the interior thereof.

In another embodiment of the invention, the structures include active substances. Active substances in the meaning of the invention are substances which—occurring or added in relatively small amounts—are capable of developing physiological effects. Examples of such active substances are hormones, vitamins, enzymes, trace elements, pharmaceutical agents, feed additives, fertilizers, pesticides, etc.

Inter alia, the active substances in the meaning of the invention can have qualitative or quantitative effects, be it activation or inhibition, on biochemical and physiological processes in living organisms.

In another preferred embodiment of the invention, the active substances are part of the polyelectrolyte layer or lipid layer of said structures. Advantageously, it is possible in this way to incorporate lipid-soluble components, e.g. fat-soluble vitamins, at high concentrations in the nanocapsules.

In another preferred embodiment of the invention, the active substance is a catalyst, a biocatalyst, a pharmaceutical agent, an enzyme, a pharmaceutical substance, a protein, a peptide, an oligonucleotide, a sensor, nucleic acids, and/or a crystal. For example, the active substances can be entrapped in the nanocapsules, or, if liposomes are present in the nanocapsules, the above-mentioned active substances can also be entrapped in the liposomes. In this case, liposomes can be used which already include the substances to be entrapped. Methods of producing such liposomes are well-known to those skilled in the art. Substances which can be used are specified in that they must not adversely affect the integrity of the liposomes, as would be the case with detergents. Suitable substances are e.g. proteins, peptides, vitamins, hormones, carbohydrates, or nucleic acids, as well as mixtures thereof. Suitable substances also include antibiotics, fungicides and antiviral agents, cytostatic agents and immunosuppressive agents, analgetic agents, anesthetics, antidepressive agents, antidiabetic agents, antihypertensive agents, anticoagulants, antiinflammatory agents, anxiolytic, sedative, antiarrhythmic, antiarthritic active substances, bronchodilators, hypoglycemic and hypolipidemic active substances, as well as active substances to stimulate erythropoiesis and apoptosis-inducing substances. For the inclusion of cargo molecules, it is also possible to start with liposomes already including these substances or having these substances bound thereto. The entrapped or bound substances remain in the interior liposomes or in the lipid layer during all of the reaction steps.

The invention also relates to the use of the inventive nanocapsules as containers or vehicles in pharmaceutical formulations.

In particular, the coated liposomes are used as containers and vehicles for biologically active substances.

As a result of the variety of usable components, the coated liposomes and the nanocapsules free of lipids can be used in numerous applications. The use of the nanocapsules expands the spectrum of carrier materials in the sense of drug targeting, as a transfer vector, a sustained release form, or in an enzyme substitution therapy. Advantageously, the components being used can be both structure-forming and activity-bearing. In particular, the coated liposomes and the nanocapsules free of lipids can be produced using substances having an antigenic effect or substances which do not induce an immune response.

The use of the nanocapsules is made possible as a result of the advantages of the method according to the invention which, for the first time, combines the advantages of mild inclusion of active substances in liposomes with an efficient technology of coating colloidal particles, which can be implemented without using further auxiliary agents and therefore involves particular advantages in pharmaceutical uses.

Enzymatic or fluorescent properties of the nanocapsules are advantageous for use in detection systems. Suitable substances having such properties are green fluorescent protein or phycobiliproteins. Other suitable polymers can be modified using fluorescent substances. Per se, suitable methods are known to those skilled in the art and involve covalent binding of the activated fluorophore to appropriate groups in the polymer, or complex formation of fluorescent metal ions with chelating groups of the polymer.

Amongst proteins, there are polymers with enzymatic activity, such as peroxidases, phophatases, proteases, dehydrogenases, glucosidases, etc.

However, nanocapsules having such a structure can also be used in target-controlled application of drugs. These highly specific molecules therefore include particularly those capable of interacting with the surface of cells. Complementary pairs in this sense are antibodies and membrane-bound antigens, lectins or selectins, and membrane-bound glycosylations, hormones and receptors thereof, and others. The modular design of these structures is advantageous, allowing the generation of a free number of specificities on just a few coat layers on the one hand, and a highly economic use of the components ultimately determining the specificity, on the other hand. The valency of the structure that is obtained, i.e., the number of surface-bound components determining the specificity, can easily be modified by titration. A high density of these components is equivalent to high avidity, enabling stable interactions even in case of unfavorable binding constants of each single interaction, as is the case e.g. between MHC complexes and T-cell receptors.

In another advantageous embodiment of the invention, nanocapsules once formed are modified with other substances. One important variant of this embodiment is modification of the nanocapsule surface using polyethylene glycol or sugars or other polyalcohols. Such coating results in particles having improved compatibility in pharmaceutical uses. When using the structure described herein for entrapping enzymes, the architecture open to diffusion ensures high availability of the entrapped activity. In addition, the diffusion paths are extremely short in the selected micrometer and submicrometer size ranges. Other uses are in the production of microcrystals of specific sizes on a chemical or biochemical route.

In another use, particularly those enzymatically active substances are employed whose substrates and products can be exchanged through the coat layer.

Nanocapsules in the meaning of the present invention have a structure open to diffusion, allowing exchange of molecules of significant size, e.g. during dissolving of the lipid layer. However, large molecules such as enzymes can be retained by the coat layer. In other inventive uses of the nanocapsules, they are loaded with enzymes catalyzing reactions, the substrates and products of which are capable of passing through the coat layer. Compared to the prior art, this way of enveloping a biological macromolecule in nanocapsules offers the advantage of extremely short diffusion paths and an associated increase of the specific activity of the entrapped enzyme. In addition, exposure to crosslinking agents as encountered in chemical fixation can be avoided.

However, signal-generating systems such as horseradish peroxidase or alkaline phosphatase or fluorescence-labelled macromolecules having specific binding properties for other substances can also be entrapped in such nanocapsules. Such systems are suitable in the detection of said other substances, particularly in medical or biochemical diagnostics. Compared to liposomes, an advantageous fact is that nanocapsules are stable to detergents, particularly those detergents used to suppress non-specific binding in such procedures, such as Tween 20 or Triton X-100.

In one variant of this use according to the invention, the nanocapsules themselves are the carriers of the signal-generating system. Advantageously, nanocapsules are prepared wherein the polymers have fluorescent properties. To this end, fluorescent derivatives of P1 and/or P2 are used to build up the nanocapsules, or the nanocapsules are coupled covalently to fluorescent substances subsequent to their preparation.

In one inventive use of the nanocapsules, they are designed so as to specifically bind to target cells of mammals. Nanocapsules used in this sense have one or more classes of ligands on their surface, the complementary binding counterparts of which being situated on the surface of the target cells. Nanocapsules having such properties are vehicles of therapeutic agents, directing the latter to a well-defined site of action. In such a use, the inner lipid layer of the hollow spheres can be maintained if beneficial in entrapping the substance to be transported.

In one variant of this use according to the invention, the nanocapsules include substances against which an immune response is to be triggered.

In one advantageous variant of this embodiment of the invention, the nanocapsules are used to transfer active substances into the cytosol of mammal cells. These nanocapsules are designed so as to be incorporated by mammal cells via endocytosis. Nanocapsules used in this embodiment of the invention are comprised of a coat layer which can be digested by the hydrolases of the endosome. Moreover, they are produced using liposomes whose membrane is capable of fusing with that of the endocytotic vesicle. One advantage in this embodiment of the teaching according to the invention is represented by the fact that such a fusion cannot give rise to liberation of lytic endosomal activities into the interior of the cell. Nanocapsules for this purpose can be loaded with various active substances. However, the above-described path of transport is particularly advantageous in transporting biological macromolecules incapable of membrane permeation, such as proteins, peptides, antibodies, enzymes, oligonucleotides, DNA, RNA, hormones, but also antibiotics, fungicides and antiviral agents, as well as cytostatic agents.

In another advantageous embodiment of the invention, the nanocapsules are to be used in biochemical diagnostics.

In another advantageous embodiment of the invention, the nanocapsules are to be used in the production of microcrystals, herbicides, pesticides and/or pigments. For example, microcrystals in the meaning of the invention are materials consisting of one or more substances and having a microscopic order. For example, peptide molecules can be concerned. Herbicides in the meaning of the invention are substances capable of effecting a negative modification in the development of all wild and cultivated plants that are undesirable in their respective location. For example, these can be defoliants, herb-destroying agents or other substances present in the form of an aerosol, liquid or solid. The herbicides in the nanocapsules of the invention can be used in pre-seeding, pre-emergence and post-emergence of cultivated plants. The respective active substances can be selected in such a way that the nanocapsules according to the present application are incorporated in the soil or applied in the foliage area of the plant. In particular, contact herbicides are concerned in that case where the herbicides develop their effect directly at the site of contact. Specifically, the following can be used: inhibitors of photosynthesis, respiration, growth substances, germination, carotene synthesis, and others. Pesticides in the meaning of the invention are all formulations capable of neutralizing or destroying all harmful or offensive organisms or prevent exposure thereto. For example, these may include agents against flies, horseflies, mosquitoes, cockroaches, bedbugs, or fleas etc., as well as products to be used against rats, mice, beetles, or moths. Pigments in the meaning of the invention are essentially insoluble, inorganic or organic, colored or non-colored dyes.

The invention also relates to a device for the continuous coating of liposomes in multiple polyelectrolyte layers, wherein a mixer is provided in the main flow of the liposomes effected by a pump, downstream of an attenuator for each separately supplied inflow of required polyelectrolyte effected by a pump, one timing element at a time being arranged between the mixers, and one attenuator at a time being arranged between the pumps for polyelectrolyte feeding and the mixers.

Accordingly, the teaching of the invention incorporates an apparatus for the continuous coating of liposomes with multiple polyelectrolyte coats. A pump allows for constant flow of the liposome solution within a tube system. The polyelectrolytes used for coating are introduced successively into the tube system as shown in FIG. 1. Mixing of the reactants is effected by strong flow or using dynamic or static mixers in the feed points. The volume of the tube sections between the individual mixing points is dimensioned such that, at a given flow rate, sufficient reaction time is available until the next mixing point is reached.

In a special embodiment, the device can be of such a design that the tube line constitutes the timing element.

The nanocapsules according to the present invention involve several advantages; they are hydrophilic, permeable and detergent-stable structures of crosslinked polymers, which, as a result of the variety of usable components, can be specified for a large number of applications. The present invention considerably expands the spectrum of substances which can be used as carrier materials in the sense of drug targeting, as a transfer vector, a sustained release form, or in an enzyme substitution therapy. The components being used can be both structure-forming and activity-bearing. The hollow spheres described can be produced using substances having an antigenic effect or substances which do not induce an immune response.

Surprisingly, it has been found that the method according to the present application, which has many advantages compared to the prior art, allows for virtually complete binding of the employed polymer to the liposomes when using suitable mass ratios, so that separation steps between single coatings are no longer required. This fact crucially contributes to the process economy of the method The suitable quantity of layer material required each time roughly corresponds to the maximum amount bound under the given reaction conditions and can be derived therefrom.

To determine the suitable amount of polyelectrolyte for each particle, increasing amounts of polymer are titrated to a supplied suspension of particles in small batches, and the size of the particles is determined thereafter. The size of the liposomes rapidly increases by formation of aggregates with the polymer to exceed a maximum. When the size with increasing amounts of polymer comes back to its original value, the optimum amount suitable for coating is used.

Surprisingly, a number of polymers, particularly proteins, were found to have a low tendency of forming aggregates. Using these materials, particles of any coating stage, i.e., template particles or species already coated can be subjected to an initial coating in such a way that recharging does not yet occur. Recharging then is achieved by addition of the same, or an equally charged, yet materially different polyelectrolyte. In this way, individual layers can be doped somewhat with activity-bearing molecules. The well-dosed use of specifically binding components permits variation of the binding strength of the particle.

One important variant of the teaching of the invention is that liposomes are contacted with polyelectrolytes of complementary charge as early as during the process of their formation. Such liposomes comprise entrapped polyelectrolyte molecules, as well as polyelectrolyte molecules adhering to the outside. The aggregation tendency decreases with the concentration of polyelectrolyte, and it is preferred to use less than 500 µg/mg lipid, more preferably less than 150 µg protein/mg lipid.

In dilute suspensions according to the above-described preferred concentrations, such particles are stable for from several minutes to hours and can be coated further according to the method of the invention. It is an advantageous effect that separation or washing steps neither are required when entrapping active substances.

Surprisingly, it has also been found that the amount of deposited polymer and thus, the density of the generated layers can be controlled via the density of charge carriers on the liposome.

Another advantage over the prior art is that the undesirable process of aggregate formation can be suppressed by high-speed mixing of the reactants and by using suitable dilutions. Another advantage is that the density of the liposomal charge carriers can be determined via the maximum salt concentration of the solution.

In familiar processes, massive formation of aggregates occurs during the production of such mixtures, resulting in flocculation of the reactants. Advantageously, this undesirable process can be suppressed by high-speed mixing of the reactants, by using suitable dilutions, and by the immediate succession of the individual steps.

Without intending to be limiting, the invention will be explained in more detail with reference to the following examples.

EXAMPLES

Abbreviations

| | |
|---|---|
| CTAB | Cetyltrimethylammonium bromide |
| FITC | Fluorescein isothiocyanate |
| PC | Phosphatidyl choline |
| MES | 2-(N-Morpholino)ethanesulfonic acid |
| PSS | Polystyrenesulfonic acid |
| PEI | Polyethyleneimine |
| DPPC | Dipalmitoylphosphatidyl choline |
| DPPG | Dipalmitoylphosphatidyl glycerol |
| DOPE | Dioleoylphosphatidyl ethanolamine |
| CHEMS | Cholesterol hemisuccinate |
| HEPES | N-(2-Hydroxyethyl)piperazine-N'-(2-ethanesulfonic acid |
| PLL | Poly-L-lysine |
| PAS | Polyacrylic acid |
| BSA | Bovine serum albumin |

Example 1

Nanocapsules Made of Polystyrenesulfonic Acid and Polyethyleneimine

Preparation of the Liposomes 400 mg of PC from soy and 9.7 mg of CTAB are dissolved in ethanol and evaporated to dryness under vacuum. The lipid film is subsequently rehydrated using a buffer (10 mM MES, 150 mM NaCl, pH 6.5). Thereafter, the suspension is pressed repeatedly through isoporous polycarbonate membranes having a pore size of 0.2 μm.

Coating with PSS

PSS (Mr 70,000) is dissolved in MES buffer (10 mM, pH 6.5) at a concentration of 10 μg/ml. The liposomes are diluted with the same buffer so as to make a lipid concentration of 200 μg/ml. Equal volumes of the two solutions are combined with stirring. Subsequently, the suspension is concentrated using tangential dialysis.

Coating with PEI

PEI (Mr 60,000) is dissolved in MES buffer (10 mM, pH 6.5) at a concentration of 5 μg/ml. The PSS-coated liposomes are diluted with the same buffer so as to make a lipid concentration of 200 μg/ml. Equal volumes of the two solutions are combined with stirring. Subsequently, the suspension is concentrated using tangential dialysis.

Further coatings can be coated as in the two steps above. The amount of polymer used binds with sufficient completeness to the particle surface, so that no purification steps have to be effected in between.

Example 2

Analysis of the Structures Having Formed

The intensity of the scattered light generated by a particle suspension is measured in a dynamic light scattering apparatus. Following addition of detergent, the measured intensity with liposomes drops to less than 5% of the initial value. After coating with three or more polymer layers, more than 40% of the intensity remains.

The stability of the thus-obtained hollow spheres free of liposomes is tested by adding NaCl. The particles are stable at least to 1 M NaCl.

Example 3

Stability of the Structures in Serum

That coated liposomes of Example 1 are concentrated by ultrafiltration to make a lipid concentration of 1 mg/ml and subsequently mixed with an equal amount of human serum. The intensity of the light scattered by the particle suspension is measured in a dynamic light scattering apparatus. At the same time, the size of the particles is determined. 24 hours after addition of serum, more than 90% of the particles having their initial size can be detected.

Example 4

Preparation of Fluorescent Nanocapsules

Modification of PEI 100 mg of PEI is dissolved in 10 ml of borate buffer (0.1 M, pH 9.0) and added with 1 ml of fluorescein isothiocyanate (10 mg/ml in dimethylformamide). The mixture is incubated at room temperature overnight. Fluorescent PEI is purified using gel filtration on Sephadex G-25®. A buffer comprised of 10 mM MES and 150 mM NaCl, pH 6.5, is used to elute the column. The eluted PEI can be detected via its scattered light in a dynamic light scattering apparatus, and the fluorescein label is detected using the absorption thereof. Fractions including a constant ratio of fluorescein and PEI are combined and used in subsequent coating.

The liposomes are prepared as in Example 1.

Coating with PSS is effected as in Example 1.

Coating with Modified PEI

Fluorescein-labelled PEI is dissolved in MES buffer (10 mM, pH 6.5) at a concentration of 10 μg/ml. The PSS-coated liposomes are diluted in the same buffer so as to make a lipid concentration of 200 μg/ml. Equal volumes of the two solutions are combined with stirring. Subsequently, the suspension is concentrated using tangential dialysis.

Further coatings can be coated as in the two steps above. The amount of polymer used binds with sufficient completeness to the particle surface, so that no purification steps have to be effected in between.

Example 5

Inclusion of a Fluorescent Cargo

Preparation of the Liposomes 400 mg of PC from soy and 9.7 mg of CTAB are dissolved in ethanol and evaporated to dryness under vacuum. The lipid film is subsequently rehydrated using a carboxyfluorescein solution (100 mM carboxyfluorescein, 10 mM MES, 150 mM NaCl, pH 6.5). Thereafter, the suspension is pressed repeatedly through isoporous polycarbonate membranes having a pore size of 0.2 μm. Non-entrapped carboxyfluorescein is removed by gel filtration on Sephadex® G25.

Coating

The liposomes are coated with PSS and PEI as in Example 1. A total of five layers is coated, the outer and inner layers consisting of PSS.

Example 6

Coating with PLL as a Function of Liposomal Charge Density

Preparation of the Liposomes 10-100 mole-% DPPG and supplementing amounts of DPPC are dissolved in isopropanol and evaporated to dryness under vacuum. The lipid film is subsequently rehydrated using an amount of buffer (10 mM HEPES, 150 mM NaCl, pH 7.5) so as to make a lipid concentration of 25 mM. The suspension is frozen at least once, thawed at 50° C. and subsequently pressed repeatedly through isoporous polycarbonate membranes having a pore size of 200 nm.

Coating with PLL and Analyzing the Structures

Figure 2:
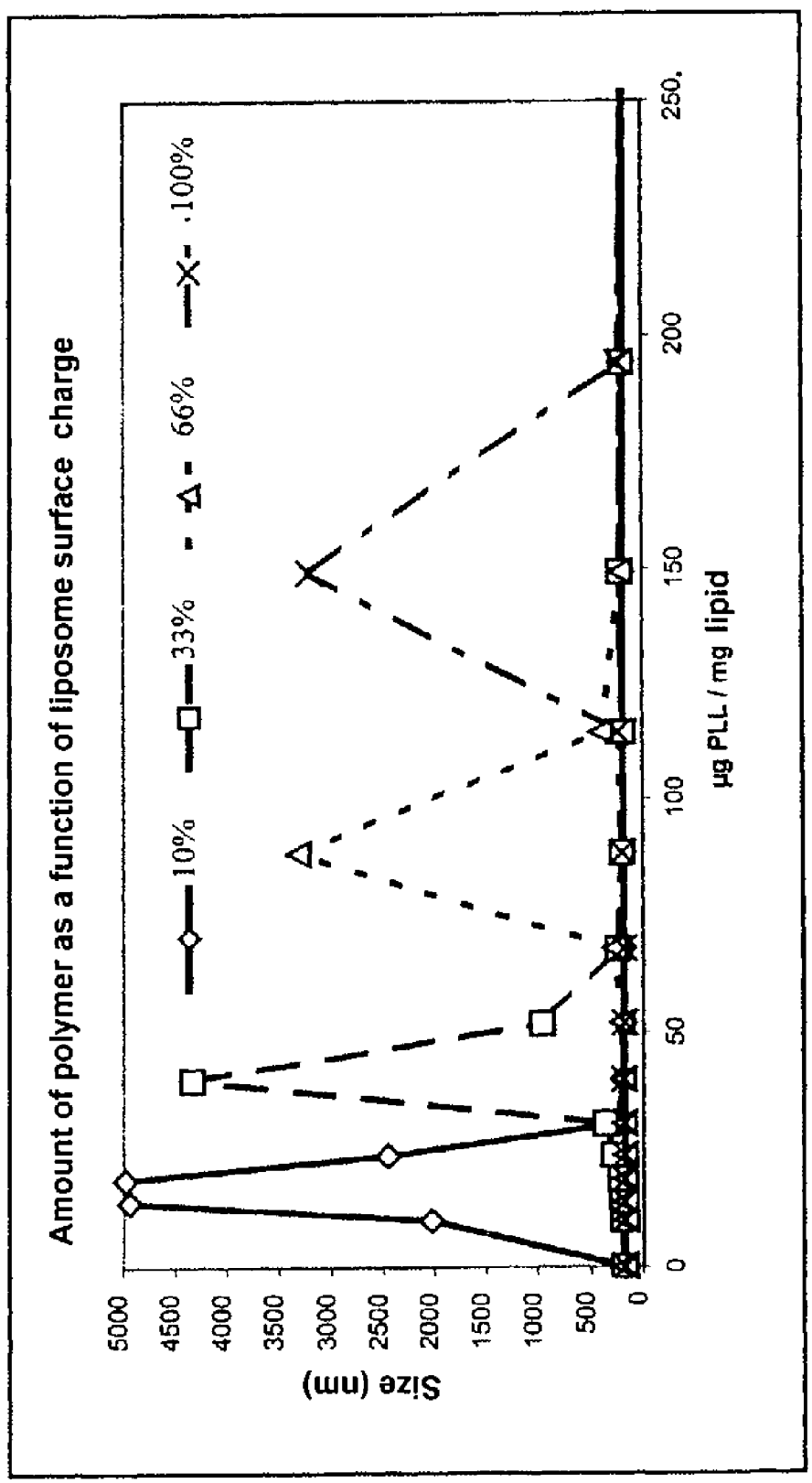
FIG. 2 graft measuring the amount of polymer as a function of liposome surface charge.

PLL (70-150 kDa) is dissolved in buffer (10 mM HEPES, pH 7.5) at a concentration of 1 mg/ml. Various liposomal formulations are diluted in buffer (10 mM HEPES, pH 7.5) to a lipid concentration of 0.2 mM. From 0 to 250 µg PLL/mg lipid is supplied in a volume of 0.2 ml at maximum and added with 10 ml of liposomal formulation with agitation. Thereafter, the structures having formed are measured using dynamic light scattering (see FIG. 2). The size of the liposomes rapidly increases by formation of aggregates with the polymer to exceed a maximum. When the size with increasing amounts of polymer comes back to its original value, the optimum amount suitable for coating is used.

Example 7

Coating with PLL as a Function of Salt Concentration

Preparation of the Liposomes

As in Example 6, and as a supplement, liposomes are also prepared using 0 . . . 40% CHEMS and supplementing amounts of DPPC.

Coating with PLL and Analyzing the Structures Formed

PLL is dissolved in buffer (10 mM HEPES pH 7.5) at suitable concentrations (0-230 µg/ml). The liposomal formulations are diluted in buffer (10 mM HEPES, pH 7.5) to a lipid concentration of 0.2 mM. Sodium chloride solutions of from 0 to 5 M in buffer (10 mm HEPES, pH 7.5) are prepared. A polymer/salt matrix is built up in 96-well microtiter plates using 30 µl of the various PLL or NaCl solutions each time. Each well of a plate is added with 240 µl of a liposomal formulation, and the turbidity is measured at 405 nm after 10 minutes.

The following table specifies the suitable amount of polymer (µg PLL/mg lipid) required to generate stable, non-aggregated structures.

Salt Stability of PLL-coated Liposomes

Liposomes coated at a particular salt concentration with a suitable amount of PLL, so as to obtain stable structures, are unstable with increasing salt concentration, forming aggregates.

Example 8

Nanocapsules Made of Albumin and Heparin

Preparation of the Liposomes 20 mole-% DPPC and 80 mole-% DPPG are dissolved in isopropanol and evaporated to dryness under vacuum. The lipid film is subsequently rehydrated using an amount of buffer (10 mM HEPES, 150 mM NaCl, pH 7.5) so as to make a lipid concentration of 25 mM. The suspension is frozen at least once, thawed at 50° C. and subsequently pressed repeatedly through isoporous polycarbonate membranes having a pore size of 200 nm.

Coating with Albumin and Heparin and Analyzing the Structures

The polymers are dissolved in buffer (10 mM sodium acetate, pH 4) at concentrations of 1 mg/ml and 5 mg/ml. The liposomes are diluted in buffer (10 mM sodium acetate, pH 4) to a lipid concentration of 0.2 mM. 50 ml of the diluted liposomes are mixed successively with suitable amounts of the two polymers (see Table). The amounts of polymer used each time bind with sufficient completeness to the particle surface, so that no purification steps have to be effected in between.

| Layer (S) | mg polymer/mg lipid |
| --- | --- |
| S1 BSA | 1.00 |
| S2 Heparin | 0.33 |
| S3 BSA | 4.75 |
| S4 Heparin | 1.59 |
| S5 BSA | 12.66 |
| S6 Heparin | 4.22 |

Crosslinking of the Structures Having Formed Using Glutaraldehyde, and Concentrating For crosslinking, the structures obtained are added with glutaraldehyde. The reaction proceeds over 2 hours at 37° C. and at a final concentration of 0.15% glutaraldehyde. Thereafter, the solution is adjusted to pH 7.5 using 1 M NaOH. Subsequently, the suspension is dialyzed against 100 mM NaCl using tangential dialysis and then concentrated.

| Liposomal charge carrier | Salt concentration | | | | | | |
| --- | --- | --- | --- | --- | --- | --- | --- |
| | 10 mM | 25 mM | 50 mM | 75 mM | 100 mM | 150 mM | 300 mM |
| 10% DPPG | 25 | 100 | Aggr. | Aggr. | Aggr. | Aggr. | Aggr. |
| 33% DPPG | 60 | 100 | 130 | 130 | 150 | 250 | Aggr. |
| 66% DPPG | 130 | 150 | 150 | 150 | 150 | 170 | Aggr. |
| 100% DPPG | 220 | 230 | 230 | 230 | 250 | 270 | >300 |
| 10% CHEMS | 25 | Aggr. | Aggr. | Aggr. | Aggr. | Aggr. | Aggr. |
| 20% CHEMS | 25 | 70 | Aggr. | Aggr. | Aggr. | Aggr. | Aggr. |
| 30% CHEMS | 60 | 70 | 100 | 250 | Aggr. | Aggr. | Aggr. |
| 40% CHEMS | 70 | 110 | 115 | 140 | 240 | Aggr. | Aggr. |

Salt Stability of the Crosslinked Structures

The stability of the structures obtained is tested by adding NaCl. The particles are stable at least to 150 mM NaCl.

Example 9

Nanocapsules Made of PLL and PAS

Preparation of the Liposomes 60 mole-% DOPE and 40 mole-% CHEMS are dissolved in isopro-panol/chloroform (3:1) and evaporated to dryness under vacuum. The lipid film is subsequently rehydrated using an amount of buffer (10 mM HEPES, 150 mM NaCl, pH 7.5) so as to make a lipid concentration of 25 mM. The suspension is frozen at least once, thawed at RT and subsequently pressed repeatedly through isoporous polycarbonate membranes having a pore size of 200 nm.

Coating With PLL and PAS and Analyzing the Structures

PLL (Mr 70 . . . 150 kDa) and PAS (Mr 30 kDa) are dissolved in buffer (10 mM HEPES, 100 mM NaCl, pH 7.5) at concentrations of 1 mg/ml and 5 mg/ml. The liposomes are diluted in buffer (10 mM HEPES, 100 mM NaCl, pH 7.5) to a lipid concentration of 0.2 mM. To produce the first layer, 130 µg PLL/mg lipid is supplied in a volume of 1 ml at maximum and 50 ml of the liposomes are injected. To produce the second layer, 55 µg PAS/mg lipid is supplied and the PLL-coated liposomes are injected. An analogous procedure is used for the following layers (see Table). The amounts of polymer used each time bind with sufficient completeness to the particle surface, so that no purification steps have to be effected in between.

| Layer (S) | µg polymer/mg lipid |
| --- | --- |
| S1 PLL | 130 |
| S2 PAS | 55 |
| S3 PLL | 200 |
| S4 PAS | 200 |
| S5 PLL | 850 |
| S6 PAS | 800 |

Crosslinking of the Structures Having Formed Using EDC, and Concentrating

For crosslinking, the structures having formed are added with EDC. The reaction proceeds over 12 hours at RT and at a final concentration of 50 mM EDC. Thereafter, the crosslinking reaction is quenched using potassium acetate (final concentration 100 mM). Subsequently, the suspension is diatangential using tangential dialysis and then concentrated.

Salt Stabiliity of the Crosslinked Structures

The stability of the structures obtained is tested by adding NaCl. The particles are stable at least to 150 mM NaCl.

Example 10

Tolerability of the Structures in Pharmaceutical Uses

Liposomes with chemically crosslinked polyelectrolyte coats are produced as in Example 8 or 9.

Wistar rats (male, 250 . . . 300 g) are kept using a regular day-night rhythm and feeding ad libitum. Two animals at a time are anesthetized, receiving 500 µl of particle suspension via the tail vein. The animals are observed for various periods of time and subsequently decapitated and disscted.

For injection, the following was used specifically: Example 8, S4 and S5, and Example 9, S6.

All of the treated animals survived the injection for at least 24 hours. None of the animals exhibited a behavior deviating from normal. Likewise, no lesions in the organs were detected.

Example 11

Coating of an Emulsion 2 g of olive oil, 8.5 g of water, 120 mg of phosphatidyl choline, and 250 mg of glycerol are mixed and stirred for two hours. Subsequently, the emulsion is homogenized in an ultrasonic bath and extruded once through a polycarbonate filter having a pore width of 200 nm. An emulsion with a mean particle size of 315 nm is formed.

PLL (70-150 kDa) is dissolved in buffer (10 mM HEPES, pH 7.5) at a concentration of 1 mg/ml.

40 µl of emulsion is diluted in 10 ml buffer (10 mM HEPES, pH 7.5). From 0 to 50 µg of PLL is supplied and added with 1 ml of emulsion with agitation. Thereafter, the structures having formed are measured using dynamic light scattering. The size of the particles rapidly increases by formation of aggregates with the polymer to exceed a maximum. When the size with increasing amounts of polymer comes back to its original value, the optimum amount suitable for coating is used. Suitable amounts of other polyelectrolytes for subsequent build-up of layers are likewise determined using this method.

With reference to the drawing, the device of the invention in one embodiment will be illustrated in more detail below. The drawing represents the basic structure of the device in a block diagram.

The main flow section of the nano- or template particles to be coated is formed by a pump 10 effecting said main flow, an attenuator 20 arranged downstream of said pump, and mixers 30, 31, 32, 33, 34, 3X, one timing element 42, 43, 44, 45, 4X at a time being arranged between said mixers.

Each influx section for feeding the respective polyelectrolytes A, B, C, D, E, X is formed by pumps 11, 12, 13, 14, 15, 1X, and attenuators 21, 22, 23, 24, 25 and 2X, respectively, arranged between the pumps and mixers 30, 31, 32, 33, 34, and 3X, respectively.

The respective modules (pumps, attenuators, mixers, and timing elements) are connected in their arrangement by means of tube lines. The volumes of the respective tube lines between mixers 30 and 31, 31 and 32, 32 and 33, 33 and 34, 34 and 3X, respectively, form the timing elements 41, 42, 43, 44, 45, and 4X, respectively. The device can be expanded at will by lining up additional influx sections (represented by dotted lines in the drawing).

To coat liposomes with multiple polyelectrolyte coats, the liposome solution is passed through the device at constant flow using a pump. The polyelectrolytes used in coating are introduced successively into the system of the main flow section. Mixing of the reactants is effected by means of mixers 30, 31, 32, 33, 34, 3X at the feeding points. The volume of the tube lines between each single mixer 30 to 3X is dimensioned such that, at a given flow rate, sufficient reaction time is available until the next mixer is reached.

The invention claimed is:

1. A method for the non-discontinuous production of microcapsules having a diameter of from 20 nm to 40 μm, comprising the steps of,
    providing a suspension of template particles in an aqueous medium,
    adding a first polyelectrolyte coating having a complementary charge with respect to the template particles to the suspension in a first amount equivalent to a titration point at which said first amount essentially binds completely to the surface of the template particles to form a first coating layer and an aggregate-free suspension, and
    without performing a separating, filtering or washing step, adding to the suspension at least one additional polyelectrolyte coating having a complementary charge with respect to the first polyelectrolyte, in an additional amount equivalent to a titration point at which said additional amount essentially binds completely to the surface of the first coating layer to form an additional coating layer and an aggregate-free suspension.

2. The method according to claim 1, wherein a chemical crosslinker is added during a coating reaction or subsequent to completion thereof linking reactive groups between the first and at least one additional polyelectrolytes.

3. The method according to claim 1, wherein the template particles have a size of between 20 nm and 1000 nm.

4. The method according to claim 1, wherein two or more dissimilar polyelectrolytes are coated simultaneously or successively in one layer.

5. The method according to claim 1, wherein the aqueous medium comprises a salt concentration of more than 50 mM.

6. The method according to claim 1, wherein the template particles are liposomes.

7. The method according to claim 6, wherein the liposomes are dissolved subsequent to adding of a last coating.

8. The method according to claim 6, wherein the liposomes have active substances entrapped therein.

9. The method according to claim 6, wherein the liposomes comprise one or more selected from the group consisting of phosphatidyl serine, phosphatidyl glycerol, phosphatidyl inositol, phosphatidic acid, sphingolipids, ceramides, tetraether lipids, cholesterol sulphate, cholesterol hemisuccinate, dimethylaminoethylcarbamoylcholesterol, alkylcarboxylic acids, alkylsulfonic acids, alkylamines, alkylammonium salts, dialkylamines, N-[1-(2,3-dioleoyloxypropyl]-N,N,N-trimethylammonium chloride, phosphoric esters with long-chain alcohols, phosphatidyl choline, phosphatidyl ethanolamine, and a-tocopherol.

10. The method according to claim 1, wherein the steps of adding polyelectrolytes is performed at a lipid concentration lower than 2 mM.

11. The method according to claim 6, wherein the liposomes comprise 10 to 50 mole of charged sterols.

12. The method according to claim 6, wherein the liposomes comprise more than 10 mole-% of phospholipids.

13. The method according to claim 6, wherein the lipid membrane is present above its respective phase transition temperature.

14. The method according to claim 1, wherein active substances are situated in the interior of said microcapsules.

15. The method of claim 1, further comprising at least one additional adding step of, without performing a separating, filtering or washing step, adding to the suspension a further polyelectrolyte coating having a complementary charge with respect to the previously added polyelectrolyte, in an additional amount equivalent to a titration point at which said additional amount essentially binds completely to the surface of a previous coating layer, to form an additional coating layer and an aggregate-free suspension.

16. The method of claim 15, wherein a chemical crosslinker is added during at least one of the further adding steps.

* * * * *